United States Patent
Sterk

(10) Patent No.: US 7,186,710 B2
(45) Date of Patent: Mar. 6, 2007

(54) PHTHALAZINONES

(75) Inventor: Geert Jan Sterk, Stadhouderslaan (NL)

(73) Assignee: Altana Pharma AG, Constance (DE)

( * ) Notice: Subject to any disclaimer, the term of this patent is extended or adjusted under 35 U.S.C. 154(b) by 299 days.

(21) Appl. No.: 10/475,657

(22) PCT Filed: Apr. 23, 2002

(86) PCT No.: PCT/EP02/04438

§ 371 (c)(1),
(2), (4) Date: Oct. 23, 2003

(87) PCT Pub. No.: WO02/085906

PCT Pub. Date: Oct. 31, 2002

(65) Prior Publication Data

US 2004/0127707 A1    Jul. 1, 2004

(30) Foreign Application Priority Data

Apr. 25, 2001   (EP) ................. 01110228

(51) Int. Cl.
- A01N 43/00 (2006.01)
- A01N 43/58 (2006.01)
- A01N 43/60 (2006.01)
- A61K 31/55 (2006.01)
- A61K 31/535 (2006.01)

(52) U.S. Cl. ............... 514/217.07; 514/234.5; 514/248; 540/599; 544/116; 544/119; 544/237

(58) Field of Classification Search ............ None
See application file for complete search history.

(56) References Cited

U.S. PATENT DOCUMENTS

| | | | |
|---|---|---|---|
| 5,716,954 A | 2/1998 | Wilhelm et al. | 514/234.2 |
| 5,859,008 A | 1/1999 | Jonas et al. | 514/222.5 |
| 6,103,718 A | 8/2000 | Sterk | 514/234.3 |
| 6,255,303 B1 | 7/2001 | Sterk | 514/222.5 |
| 6,380,196 B1 | 4/2002 | Ulrich et al. | 514/248 |
| 6,544,993 B1 | 4/2003 | Sterk | 514/248 |

FOREIGN PATENT DOCUMENTS

| | | |
|---|---|---|
| EP | 0763534 | 9/1996 |
| EP | 0934933 | 8/1999 |
| WO | WO 93/07146 | 4/1993 |
| WO | WO 94/12461 | 6/1994 |
| WO | WO 98/31674 | 7/1998 |
| WO | WO 99/31071 | 6/1999 |
| WO | WO 99/31090 | 6/1999 |
| WO | WO99/47505 | 9/1999 |
| WO | WO 01/19818 | 3/2001 |
| WO | WO 01/30766 | 5/2001 |
| WO | WO 01/30777 | 5/2001 |
| WO | WO 01/94319 | 12/2001 |

OTHER PUBLICATIONS

Huang et al, "The Next Generation of PDE4 Inhibitors" Current Opinion in Chemical Biology, vol. 5, pp. 432-438 (2001).*
Dyke and Montana "The therapeutic potential of PDE4 inhibitors" Expert Opinion on Investigational Drugs, vol. 8(9), pp. 1301-1325 (1999).*
Van der Mey, et al., "Novel Selective PDE4 Inhibitors. 1. Synthesis, Structure—Activity Relationships, and Molecular Modeling of 4-(3,4-dimethoxyphenyl)-2H phthalazin-1-ones and Analogues", J. Med. Chem., 44, p. 2511-2522 (2001).
Van der Mey, et al., "Novel Selective PDE4 Inhibitors. 2. Synthesis and Structure—Activity Relationships of 4-Aryl-Substituted cis-tetra and cis-Hexahydrophthalazinones", J. Med. Chem., 44, p. 2523-2535 (2001).
Van der Mey, et al., "Novel Selective PDE4 Inhibitors. 3. In vivo Antiinflammatory Activity of a New Series of N-Substituted cis-Tetra and cis-Hexahydrophthalazinones", J. Med. Chem., 45, p. 2520-2525 (2002).
Van der Mey, et al., "Novel Selective Phosphodiesterase (PDE4) Inhibitors. 4. Resolution, Absolute Configuration and PDE4 Inhibitory Activity of cis-Tetra and cis-Hexahydrophthalazinones", J. Med. Chem., 45, p. 2526-2533 (2002).
Dal Piaz V., et al. "Novel Heterocyclic Fused Pyridazinones as Potent and Selective Phosphodiesterase IV Inhibitors", J. Med. Chem., 40, p. 1417-1421 (1997).
Thornber, C.W., "Isosterism and Molecular Modification in Drug Design", Chem. Soc. Reviews, pp. 563-579 (1979).

* cited by examiner

Primary Examiner—Zachary C. Tucker
(74) Attorney, Agent, or Firm—Nath & Associates PLLC; Joshua B. Goldberg; Sheldon M. McGee

(57) ABSTRACT

The compounds of formula I

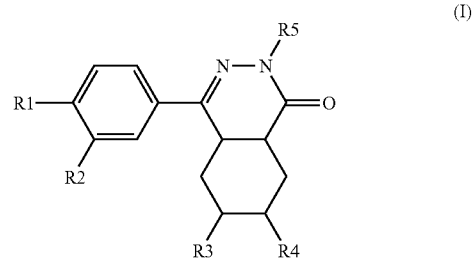

in which R1, R2, R3, R4 and R5 have the meanings as given in the description are PDE4/7 inhibitors.

14 Claims, No Drawings

PHTHALAZINONES

This application was filed under 35 U.S.C. 371 and is the U.S. national stage of PCT/EP02/04438, filed Apr. 23, 2002.

FIELD OF APPLICATION OF THE INVENTION

The invention relates to novel phthalazinone-derivatives, which are used in the pharmaceutical industry for the production of medicaments.

KNOWN TECHNICAL BACKGROUND

International Patent Applications WO98/31674, WO99/31071, WO99/31090 and WO99/47505 disclose phthalazinone derivatives having selective PDE4 inhibitory properties. In the International patent application WO01/19818 phthalazinone derivatives with PDE3/4 inhibitory properties are disclosed. In the International Patent Application WO94/12461 and In the European Patent Application EP 0 763 534 3-aryl-pyridazin-6-one and arylalkyl-diazinone derivatives are described as selective PDE4 inhibitors.

DESCRIPTION OF THE INVENTION

It has now been found that the phthalazinone-derivatives, which are described in greater details below, have surprising and particularly advantageous properties.

The invention thus relates to compounds of formula I

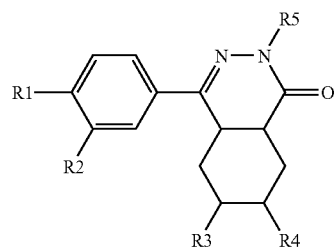

(I)

in which
R1 is 1-2C-alkoxy or 1-2C-alkoxy which is completely or predominantly substituted by fluorine,
R2 is fluorine, bromine or chlorine,
R3 and R4 are both hydrogen or together form an additional bond,
R5 is R6, —$C_mH_{2m}$—R7, —$C_nH_{2n}$—C(O)R8, —CH(R9)$_2$, —$C_pH_{2p}$—Y—Aryl1, R12 or R26, in which
R6 1-8C-alkyl, 3-10C-cycloalkyl, 3-7C-cycloalkylmethyl, 3-7C-alkenyl, 3-7C-alkinyl, phenyl-3-4C-alkenyl, 7-10C-polycycloalkyl, naphthyl, pyridyl, pyrazinyl, pyridazinyl, pyrimidyl, quinazolinyl, quinoxalinyl, cinnolinyl, isoquinolinyt, quinolinyl, indanyl, indazolyl, benzoxazolyl, benzothiazolyl, oxazolyl, thiazolyl, N-methylpiperidyl, tetrahydropyranyl, 6-methyl-3-trifluoromethyl-pyridin-2-yl, 1,3,4-trimethyl-1H-pyrazolo[3,4-b]pyridin-6-yl, 3-thiophen-2-yl[1,2,4]thiadiazol-5-yl, 1,1-dioxide-tetrahydrothlophen-3-yl, 1-oxo-1,3-dihydro-isobenzofuran-5-yl, 4-(4yl-but-1-oxy)-benzoic acid, or an unsubstituted or by R61 and/or R62 substituted phenyl radical, in which
R61 is hydroxyl, 1-4C-alkyl, 1-4C-alkoxy, nitro, cyano, halogen, carboxyl, hydroxycarbonyl-1-4C-alkyl, 1-4C-alkoxycarbonyl, hydroxy-1-4C-alkyl, amino, mono- or di-1-4C-alkylamino, 1-4C-alkylcarbonylamino, aminocarbonyl, mono- or di-1-4C-alkylaminocarbonyl, aminosulfonyl, mono- or di-1-4C-alkylaminosulfonyl, 4-methylphenylsulfonamido, imidazolyl, tetrazol-5-yl, 2-(1-4C-alkyl)tetrazol-5-yl or 2-benzyl-tetrazol-5-yl and
R62 is 1-4C-alkyl, 1-4C-alkoxy, nitro or halogen,
R7 is hydroxyl, halogen, cyano, nitro, nitroxy(—O—NO$_2$), carboxyl, carboxyphenyloxy, phenoxy, 1-4C-alkoxy, 3-7C-cycloalkoxy, 3-7C-cycloalkylmethoxy, 1-4C-alkylcarbonyl, 1-4C-alkylcarbonyloxy, 1-4C-alkylcarbonylamino, 1-4C-alkoxycarbonyl, aminocarbonyl, mono- or di-1-4C-alkylaminocarbonyl, amino, mono- or di-1-4C-alkylamino, or an unsubstituted or by R71 and/or R72 substituted piperidyl, piperazinyl, pyrrolidinyl or morpholinyl radical, where
R71 is hydroxyl, 1-4C-alkyl, hydroxy-1-4C-alkyl or 1-4C-alkoxycarbonyl, and
R72 is 1-4C-alkyl, carboxyl, aminocarbonyl or 1-4C-alkoxycarbonyl,
R8 is an unsubstituted or by R81 and/or R82 substituted phenyl, naphthyl, phenanthrenyl or anthracenyl radical, in which
R81 is hydroxyl, halogen, cyano, 1-4C-alkyl, 1-4C-alkoxy, carboxyl, aminocarbonyl, mono- or di-1-4C-alkylaminocarbonyl, 1-4C-alkylcarbonyloxy, 1-4C-alkoxycarbonyl, amino, mono- or di-1-4C-alkylamino, 1-4C-alkylcarbonylamino, or 1-4C-alkoxy which is completely or predominantly substituted by fluorine, and
R82 is hydroxyl, halogen, 1-4C-alkyl, 1-4C-alkoxy or 1-4C-alkoxy which is completely or predominantly substituted by fluorine,
R9 is —$C_qH_{2q}$-phenyl,
Y is a bond or O (oxygen),
Aryl1 is an unsubstituted phenyl, naphthyl, pyridyl, pyrazinyl, pyridazinyl, pyrimidinyl, quinazolinyl, quinoxalinyl, cinnolinyl, isoquinolyl, quinolyl, coumarinyl, benzimidazolyl, benzoxazolyl, benzothiazolyl, benzotriazolyl, N-benzosuccinlmldyl, imidazolyl, pyrazolyl, oxazolyl, thiazolyl, furyl, thienyl, pyrrolyl, a 2-(1-4C-alkyl)-thiazol-4-yl radical, or a phenyl radical substituted by R10 and/or R11, in which
R10 is hydroxyl, halogen, nitro, cyano, 1-4C-alkyl, trifluoromethyl, 1-4C-alkoxy, carboxyl, hydroxycarbon yl-1-4C-alkyl, 1-4C-alkylcarbonyloxy, 1-4C-alkoxycarbonyl, amino, mono- or di-1-4C-alkylamino, 1-4C-alkylcarbonylamino, aminocarbonyl, mono- or di-1-4C-alkylaminocarbonyl, imidazolyl or tetrazolyl, and
R11 is hydroxyl, halogen, nitro, 1-4C-alkyl or 1-4C-alkoxy,
m is an integer from 1 to 8,
n is an integer from 1 to 4,
p is an integer from 1 to 6,
q is an integer from 0 to 2,
R12 is a radical of formula (a)

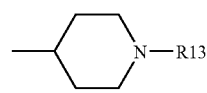

(a)

wherein
R13 is —S(O)$_2$—R14, —S(O)$_2$—(CH$_2$)$_r$—R15, —(CH$_2$)$_s$—S(O)$_2$—R16, —C(O)R17, —C(O)—(CH$_2$)$_r$—R18, —(CH$_2$)$_s$—C(O)—R19, Hetaryl1, Aryl2 or Aryl3-1-4C-alkyl, R14 is 1-4C-alkyl, 5-dimethylaminonaphthalin-1-yl, —N(R20)R21, phenyl or phenyl substituted by R22 and/or R23, R15 is —N(R20)R21, R16 is —N(R20)R21, R17 is 1-4C-alkyl, hydroxycarbonyl-1-4C-alkyl, phenyl, pyridyl, 4-ethyl-piperazin-2,3-dion-1-yl, 2-oxo-imidazolidin-1-yl or —N(R20)R21, R18 is —N(R20)R21, R19 is —N(R20)R21, phenyl, phenyl substituted by R22 and/or R23 and/or R24, R20 and R21 are independent from each other hydrogen, 1-7C-alkyl, 3-7C-cycloalkyl, 3-7C-cycloalkylmethyl or phenyl, or R20 and R21 together and with inclusion of the nitrogen atom to which they are bonded, form a 4-morpholinyl-ring, 1-pyrrolidinyl-ring, 1-piperidinyl-ring, 1-hexahydroazepino-ring or a 1-piperazinyl-ring of formula (b)

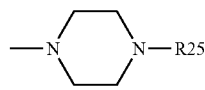

(b)

wherein

R25 is pyrid-4-yl, pyrid-4-ylmethyl, 1-4C-alkyl-dimethylamino, dimethylaminocarbonyimethyl, N-methyl-piperidin-4-yl, 4-morpholino-ethyl or tetrahydrofuran-2-ylmethyl, R22 is halogen, nitro, cyano, carboxyl, 1-4C-alkyl, trifluoromethyl, 1-4C-alkoxy, 1-4C-alkoxycarbonyl, amino, mono-or di-1-4C-alkylamino, aminocarbonyl 1-4C-alkylcarbonylamino or mono-or di-1-4C-alkylaminocarbonyl, R23 is halogen, amino, nitro, 1-4C-alkyl or 1-4C-alkoxy, R24 is halogen, Hetaryl1 is pyrimidin-2-yl, thieno-[2,3-d]pyrimidin-4-yl, 1-methyl-1H-pyrazolo-[3,4-d]pyrimidin-4-yl, thiazolyl, imidazolyl or furanyl, Aryl2 is pyridyl, phenyl or phenyl substituted by R22 and/or R23, Aryl3 is pyrldyl, phenyl, phenyl substituted by R22 and/or R23, 2-oxo-2H-chromen-7-yl or 4-(1,2,3-thladiazol4-yl) phenyl, r is an integer from 1 to 4, s is an integer from 1 to 4, R26 is a radical of formula (c)

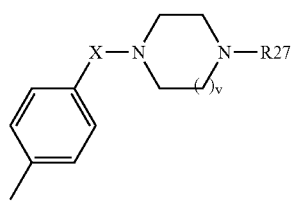

(c)

wherein

R27 is —C(O)R28, —(CH$_2$)$_t$—C(O)R29, —(CH$_2$)$_u$R30, Aryl4, Hetaryl2, phenylprop-1-en-3-yl or 1-methylpiperidin-4yl, R28 hydrogen, 1-4C-alkyl, —OR31, furanyl, indolyl, phenyl, pyridyl, phenyl substituted by R34 and/or R35 or pyridyl substituted by R36 and/or R37, R29 is —N(R32)R33, R30 is —N(R32)R33, tetrahydrofuranyl or pyridinyl, R31 is 1-4C-alkyl, R32 is hydrogen, 1-4C-alkyl, 3-7C-cycloalkyl or 3-7C-cycloalkylmethyl, R33 is hydrogen, 1-4C-alkyl, 3-7C-cycloalkyl or 3-7C-cycloalkylmethyl, or R32 and R33 together and with inclusion of the nitrogen atom to which they are bonded, form a 4-morpholinyl-, 1-pyrrolidinyl-, 1-piperidinyl- or 1-hexahydroazepinyl-ring, Aryl4 is phenyl, pyridyl, pyrimidinyl, phenyl substituted by R34 and/or R35, pyridyl substituted by R36 and/or R37, R34 is halogen, nitro, 1-4C-alkyl, trifluoromethyl or 1-4C-alkoxy, R35 is halogen or 1-4C-alkyl, R36 is halogen, nitro, 1-4C-alkyl, trifluoromethyl or 1-4C-alkoxy, R37 is halogen or 1-4C-alkyl, Hetaryl2 is indol4-yl, 2-methyl-quinolin-4-yl, 5-chloro-6-oxo-1-phenyl-1,6-dihydro-pyridazin-4-yl, 3-phenyl-1,2,4-thladiazol-5-yl or 3-o-tolyl-1,2,4-thiadiazol-5-yl, t is an integer from 1 to 4, u is an integer from 1 to 4, v is an integer from 1 to 2, X is —C(O)— or —S(O)$_2$—, and the salts of these compounds, with the proviso that the compound (cis)-4-(3-Chloro4-methoxy-phenyl)2-cycloheptyl-4a,5,8,8a-tetrahydro-2H-phthalazin-1-one is excluded.

1-8C-Alkyl is a straight-chain or branched alkyl radical having 1 to 8 carbon atoms. Examples are the octyl, heptyl, isoheptyl (5-methylhexyl), hexyl, isohexyl (4-methylpentyl), neohexyl (3,3-dimethylbutyl), neopentyl (2,2-dimethylpropyl), pentyl, isopentyl (3-methylbutyl), 1-ethylpropyl, butyl, isobutyl, sec-butyl, tert-butyl, propyl, isopropyl, ethyl and methyl radicals.

1-4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1-4C-Alkoxy is a radical, which, in addition to the oxygen atom contains a straight-chain or branched alkyl radical having 1 to 4 carbon atoms. Alkoxy radicals having 1 to 4 carbon atoms which may be mentioned in this context are, for example, the butoxy, iso-butoxy, sec-butoxy, tert-butoxy, propoxy, isopropoxy, ethoxy and methoxy radicals.

1-4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical. "Predominantly" in this connection means that more than half of the hydrogen atoms of the 1-4C-alkoxy groups is replaced by fluorine atoms.

1-2C-Alkoxy which is completely or predominantly substituted by fluorine is, for example, the 1,1,2,2-tetrafluoroethoxy, the 2,2,2-trifluoroethoxy and in particular the trifluoromethoxy and the difluoromethoxy radical.

1-8C-Alkoxy is a radical which, in addition to the oxygen atom, contains a straight-chain or branched alkyl radical having 1 to 8 carbon atoms. Alkoxy radicals having 1 to 8 carbon atoms which may be mentioned in this context are, for example, the octyloxy, heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy, isopropoxy, ethoxy and methoxy radicals.

3-7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are preferred.

3-7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopen-tylmethoxy are preferred.

3-10C-Cycloalkyl stands for cyclopropyl, cyclobutyl, cyclopentyl, cyclohexyl, cycloheptyl, cyclooctyl, cyclononyl or cyclodecyl.

3-7C-Cycloalkylmethyl stands for a methyl radical, which is substituted by one of the abovementioned 3-7C-cycloalkyl radicals. Examples which may be mentioned are the cyclopropylmethyl, the cyclopentylmethyl and the cyclohexylmethyl radicals.

3-7C-Alkenyl is a straight chain or branched alkenyl radical having 3 to 7 carbon atoms. Preferred examples are the 2-butenyl, 3-butenyl, 1-propenyl and the 2-propenyl (allyl) radicals.

3-7C-Alkinyl is a straight chain or branched alkinyl radical having 3 to 7 carbon atoms. Preferred examples are the 2-penfinyl, 2-butinyl, 3-butinyA and the 2-propinyl (propargyl) radicals.

7-10C-Polycycloalkyl stands for 7-10C-bicycloalkyl or 7-10C-tricycloalkyl radicals, such as for example, bomyl, norbornyl or adamantyl.

A Phenyl-3-4C-alkenyl radical is, for example, the phenylprop-1-en-3-yl radical.

Halogen within the meaning of the present invention is bromine, chlorine and fluorine.

1-4C-Alkylcarbonyl is a carbonyl group to which one of the abovementioned 1-4Calkyl radicals is bonded. An example is the acetyl radical [$CH_3C(O)$—].

1-4C-Alkylcarbonyloxy radicals contain, in addition to the oxygen atom, one of the abovementioned 1-4C-alkylcarbonyl radicals. An example is the acetoxy radical [$CH_3C(O)$—$O$—].

A 1-4C-Alkylcarbonylamino radical is, for example, the acetamido radical [—$NH$—$C(O)$—$CH_3$].

1-4C-Alkoxycarbonyl is a carbonyl group to which one of the abovementioned 1-4C-alkoxy radicals is bonded. Examples are the ethoxycarbonyl [$CH_3CH_2O$—$C(O)$—] and the methoxycarbonyl [$CH_3O$—$C(O)$—] radicals.

Mono- or Di-1-4C-alkylaminocarbonyl radicals are, for example, the methylaminocarbonyl, the dimethylaminocarbonyl and the diethylaminocarbonyl radicals.

Mono- or Di-1-4C-alkylamino radicals are, for example, the methylamino, the dimethylamino and the diethylamino radicals.

Mono- or Di-1-4C-alkylaminosulfonyl stands for a sulfonyl group to which one of the abovementioned mono- or di-1-4C-alkylamino radicals is bonded. Examples which may be mentioned are the methylaminosulfonyl, the dimethylaminosulfonyl and the ethylaminosulfonyl radical.

Hydroxy-1-4C-alkyl stands for one of the abovementioned 1-4C-alkyl radicals which is substituted by hydroxyl. Examples which may be mentioned are the hydroxymethyl radical, the 2-hydroxyethyl radical or the 3-hydroxypropyl radical.

Hydroxycarbonyl-1-4C-alkyl radicals are, for example, the hydroxycarbonylmethyl [—$CH_2C(O)OH$] and the hydroxycarbonylethyl [—$CH_2CH_2C(O)OH$] radicals.

If R3 and R4 together form an additional bond, then the carbon atoms to which R3 and R4 are attached are linked to one another via a double bond.

The groups —$C_mH_m$—, —$C_nH_{2n}$—, —$C_pH_{2p}$— and —$C_qH_{2q}$— can be straight chain or branched groups. Examples which may be mentioned for the —$C_mH_{2m}$— group are the octylene, heptylene, isoheptylene (2-methylhexylene), hexylene, isohexylene (2-methylpentylene), neohexylene (2,2-dimethylbutylene), butylene, isobutylene, sec-butylene, tert-butylene, propylene, isopropylene, ethylene, 1-methylmethylene and the methylene group.

Examples which may be mentioned for the —$C_pH_{2p}$— group are the hexylene, isohexylene (2-methylpentylene), neohexylene (2,2-dimethylbutylene), butylene, isobutylene, sec-butylene, tert-butylene, propylene, isopropylene, ethylene, 1-methylmethylene and the methylene group.

Examples which may be mentioned for the —$C_mH_{2m}$— group are the butylene, isobutylene, sec-butylene, tert-butylene, propylene, isopropylene, ethylene, 1-methylmethylene and the methylene group.

Examples which may be mentioned for the —$C_qH_{2q}$— group are the ethylene, 1-methylmethylene and the methylene group. The group —$C_qH_{2q}$— represents a covalent bond in case of q is 0 (zero).

Aza-heterocyles which are a component (=Aryl1) of the group of substituents defined as —$C_pH_{2p}$-Aryl1 and contain the grouping —NH— (imino), such as for example, pyrrole, imidazole, benzimidazole, benzotriazole or benzosuccinimide, are preferably bonded via their imino-nitrogen to the above defined —$C_pH_{2p}$— group.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled In the art.

According to experts knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of formula I which are to be emphasized are those in which
R1 is methoxy or ethoxy,
R2 is chlorine, bromine or fluorine
R3 and R4 together form an additional bond,
R5 is R6, —$C_mH_{2m}$—R7, —$C_pH_{2p}$—Y-Aryl1, R12 or R26 in which
R6 3-6C-cycloalkyl, 3-7C-cycloalkylmethyl, quinoxalinyl, indazolyl, benzothiazolyl, 6-methyl-3-trifluoromethyl-pyridin-2-yl, 1,3,4-trimethyl-1H-pyrazolo[3,4-b]pyridin-6-yl, 3-thiophen-2-yl[1,2,4]-thiadiazol-5-yl, 1,1-dioxide-tetrahydrothiophen-3-yl, 1-oxo-1,3-dihydro-isobenzofuran-5-yl, 4-(4-yl-but-1-oxy)-benzoic acid, or an unsubstituted or by R61 substituted phenyl radical, in which
R61 is 1-4C-alkyl, 1-4C-alkoxy, carboxyl or 1-4C-alkoxycarbonyl,
R7 is carboxyphenyloxy,
Y is a bond,
Aryl1 is imidazolyl,
m is an integer from 1 to 4,
p is an integer from 1 to 4,
R12 is a radical of formula (a)

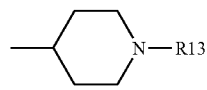 (a)

wherein
R13 is —$S(O)_2$—R14, —C(O)R17 or Aryl3-1-4C-alkyl,
R14 is phenyl or phenyl substituted by R22,
R17 is 1-4C-alkyl, 2-oxo-imidazolidin-1-yl or —N(R20)R21,
R20 and R21 are independent from each other 1-7C-alkyl, or R20 and R21 together and with inclusion of the nitrogen atom to which they are bonded, form a 4-morpholinyt, 1-pyrrolidinyl-, 1-piperidinyl- or 1-hexahydroazepino-ring,
R22 is 1-4C-alkyl,
Aryl3 is pyridyl,
R26 is a radical of formula (c)

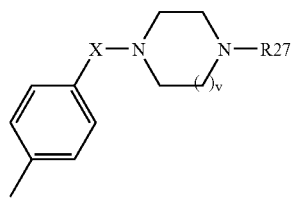 (c)

wherein
R27 is —$(CH_2)_u$R30,
R30 is —N(R32)R33,
R32 is 1-4C-alkyl,
R33 is 1-4C-alkyl,
or R32 and R33 together and with Inclusion of the nitrogen atom to which they are bonded, form a 4-morpholinyl-, 1-pyrrolidinyl-, 1-piperidinyl- or 1-hexahydroazepinyl-ring,
u is an integer from 1 to 4,
v is 1,
X is —C(O)—,
and the salts of these compounds.

Compounds of formula I which are particularly to be emphasized are those in which
R1 is methoxy or ethoxy,
R2 is chlorine, bromine or fluorine,
R3 and R4 together form an additional bond,
R5 is 1-(morpholin-4-yl-methanoyl)-piperidin-4-yl, 1-(toluene-4-sulfonyl)-piperidin-4-yl, 1-acetyl-piperidin-4-yl, 1-(pyridin-4-ylmethylypiperidin-4-yl, 4-{1-[4-(2-dimethylamino-ethyl)-piperazin-1-yl]-methanoyl}-phenyl, quinoxalin-2-yl, 6-methyl-3-trifluoromethyl-pyridin-2-yl, 1,3,4-trimethyl-1H-pyrazolo[3,4-b]pyridin-6-yl, phenyl, 3-thiophen-2-yl[1,2,4]thiadiazol-5-yl, 1,1-dioxide-tetrahydrothiophen-3yl, benzothiazol-6-yl, 1-oxo-1,3-dihydro-isobenzofuran-5-yl, 1H-indazol-5-yl, cyclopentyl, 4-imidazol-1-yl-butyl, 4-(4-yl-but-1-oxy)-benzoic acid, 4-hydroxycarbonylphenyl or 1-[1-[2-oxo-imidazolidin-1-yl)methanoyl]piperidin-4-yl, and the salts of these compounds.
Preferred compounds of formula I are those in which
R1 is methoxy or ethoxy,
R2 is chlorine,
R3 and R4 together form an additional bond,
R5 is 1-(morpholin-4-yl-methanoyl)-piperidinyl, 1-(toluene-4-sulfonyl)-piperidinyl, 1-acetyl-piperidin-4-yl, 1-(pyridin-4-ylmethyl)-piperidinyl, 4-{1-[4-(2-dimethylamino-ethyl)-piperazin-1-yl]-methanoyl}phenyl, quinoxalin-2-yl, 6-methyl-3-trifluoromethyl-pyridin-2-yl, 1,3,4-trimethyl-1H-pyrazolo[3,4-b]pyridin-6-yl, phenyl, 3-thiophen-2-yl[1,2,4]thiadiazol-5-yl, 1,1-dioxide-tetrahydrothiophen-3-yl, benzothiazol-6-yl, 1-oxo-1,3-dihydro-isobenzofuran-5-yl, 1H-indazol-5-yl, cyclopentyl, 4-imidazol-1-yl-butyl, 4-(4-yl-but-1-oxy)benzoic acid, 4-hydroxycarbonylphenyl or 1-[1-[2-oxo-imidazolidin-1-yl)methanoyl]piperidin-4-yl, and the salts of these compounds.
Further preferred compounds of formula I are
(cis)-4-(3-Chloro-4-methoxy-phenyl)-2-[1-(1-morpholin-4yl-methanoyl)-piperidin-4-yl]-4a,5,8,8a-tetrahydro-2H-phthalazin-1-one,
(cis)-4-(3-Chloro-4-methoxy-phenyl)-2-[1-(toluene-4-sulfonyl)-piperidin-4-yl]-4a,5,8,8a-tetrahydro-2H-phthalazin-1-one,
(cis)-2-(1-Acetyl-piperidin-4-yl)-4-(3-chloro-4-methoxy-phenyl)-4a,5,8,8a-tetrahydro-2H-phthalazin-1-one,
(cis)-4-(3-Chloro-4-methoxy-phenyl)-2-(1-pyridin-4-ylmethyl-piperidin-4-yl)-4a,5,8,8a-tetrahydro-2H-phthalazin-1-one,
(cis)-4-(3-Chloro-4-methoxy-phenyl)-2-(4-{1-[4-(2-dimethylamino-ethyl)-piperazin-1-yl]-methanoyl}-phenyl)-4a,5,8,8a-tetrahydro-2H-phthalazin-1-one,
(cis)-4-(3-Chloro-4-methoxy-phenyl)-2-(6-methyl-3-trifluoromethyl-pyridin-2-yl)-4a,5,8,8a-tetrahydro-2H-phthalazin-1-one,
(cis)-2-Benzothiazol-6-yl-4-(3-chloro-4-methoxy-phenyl)-4a,5,8,8a-tetrahydro-2H-phthalazin-1-one
(cis)-4-(3-Chloro-4-methoxy-phenyl)-2-(1-oxo-1,3-dihydro-isobenzofuran-5-yl)-4a,5,8,8a-tetrahydro-2H-phthalazin-1-one,
(cis)-4-(3-Chloro4-methoxy-phenyl)-2-(1H-indazol-5-yl)-4a,5,8,8a-tetrahydro-2H-phthalazin-1-one,
(cis)-4-(3-Chloro-4-methoxy-phenyl)-2-cyclopentyl-4a,5,8,8a-tetrahydro-2H-phthalazin-1-one,
(cis)-4-(3-Chloro-4-methoxy-phenyl)2-(4-imidazol-1-yl-butyl)-4a,5,8,8a-tetrahydro-2H-phthalazin-1-one, (cis)-4-{4-[4-(3-Chloro-4-methoxy-phenyl)-1-oxo-4a,5,8, 8a-tetrahydro-1H-phthalazin-2-yl]-butoxy}-benzoic acid,
(cis)-4-[4-(3-Fluoro-4-methoxy-phenyl)-1-oxo-4a,5,8,8a-tetrahydro-1H-phthalazin-2-yl]-benzoic acid,
(cis)-4-{4-(3-chloro-4-methoxyphenyl)-1-oxo-4a,5,8,8a-tetrahydro-1H-phthalazin-2-yl}benzoic acid,
(cis)-4-{4-(3-bromo-4-methoxyphenyl)-1-oxo-4a,5,8,8a-tetrahydro-2H-phthalazin-2-yl}benzoic acid,
(cis)-4-(3-chloro-4-methoxy-phenyl)-2-quinoxalin-2-yl-4a, 5,8,8a-tetrahydro-2H-phthalazin-1-one,
(cis)-4-(3-Chloro-4-methoxy-phenyl)2-(1,3,4-trimethyl-1H-pyrazolo[3,4-b]pyridin-6-yl)-4a,5,8,8a-tetrahydro-2H-phthalazin-1-one,
(cis)-4-(3-Chloro-4-methoxy-phenyl)-2-(3-thiophen-2-yl-[1,2,4]thiadiazol-5-yl)4a,5,8,8a-tetrahydro-2H-phthalazin-1-one,
(cis)-4-(3-Chloro-4-methoxy-phenyl)-2-(1,1-dioxo-tetrahydro-1l(6)-thiophen-3-yl)-4a,5,8,8a-tetrahydro-2H-phthalazin-1-one,
(cis)-4-(3-Chloro-4ethoxy-phenyl)-2-phenyl-4a,5,8,8a-tetrahydro-2H-phthalazin-1-one,
(cis)-4-(3Chloro-4-methoxy-phenyl)-2-phenyl-4a25,8,8a-tetrahydro-2H-phthalazin-1-one,
(cis)-4-(3-Chloro-4-methoxy-phenyl)-2-{1-[1-(2-oxo-imidazolidin-1-yl)-methanoyl]-piperidine-4-yl}-4a,5,8,8a-tetrahydro-2H-phthalazin-1-one, and the salts of these compounds.

A special embodiment of the compounds of the present invention include those compounds of formula I in which R1 is 1-2C-alkoxy, R2 is chlorine, R3 and R4 together form an additional bond and R5 is R6.

Another special embodiment of the compounds of the present Invention include those compounds of formula I in which R1 is 1-2C-alkoxy, R2 is chlorine, R3 and R4 together form an additional bond and R5 is —$C_mH_{2m}$—R7.

A further special embodiment of the compounds of the present Invention Include those compounds of formula I in which R1 is 1-2C-alkoxy, R2 is chlorine, R3 and R4 together form an additional bond and R5 is —$C_pH_{2p}$—Y-Aryl1.

Still another special embodiment of the compounds of the present invention include those compounds of formula I in which R1 is 1-2C-alkoxy, R2 is chlorine, R3 and R4 together form an additional bond and R5 is R12.

Yet another special embodiment of the compounds of the present Invention include those compounds of formula I in which R1 is 1-2C-alkoxy, R2 is chlorine, R3 and R4 together form an additional bond and R5 is R26.

The compounds of formula I are chiral compounds. Chiral centers exist in the compounds of formula I in the positions 4a and 8a.

Numbering

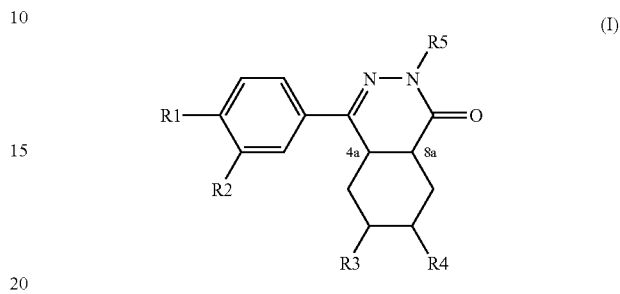

(I)

Therefore the invention includes all conceivable pure diastereomers and pure enantiomers of the compounds of formula I, as well as all mixtures thereof independent from the ratio, including the racemates. Preferred are those compounds of formula I, in which the hydrogen atoms in the positions 4a and 8a are cis-configurated. Especially preferred in this connection are those compounds, in which the absolute configuration (according to the rules of Cahn, Ingold and Prelog) is S in the position 4a and R in the position 8a.

Racemates can be split up into the corresponding enantiomers by methods known by a person skilled in the art. Preferably the racemic mixtures are separated into two diastereomers during the preparation with the help of an optical active separation agent on the stage of the cyclohexanecarboxylic acids or the 1,2,3,6-tetrahydrobenzoic acids (for example, starting compounds A5 and A6). As separation agents may be mentioned, for example, optical active amines such as the (+)- and (−)-forms of 1-phenylethylamine [(R)-(+)-1-phenylethylamine=D-α-methylbenzylamine; or (S)-(−)-1-phenylethylamine=L-α-methylbenzylamine), ephedrine, the optical active alkaloids quinine, cinchonine, cinchonidine and brucine.

The compounds according to the invention can be prepared, for example, as described in Reaction scheme 1, 2 or 3.

Reaction scheme 1:

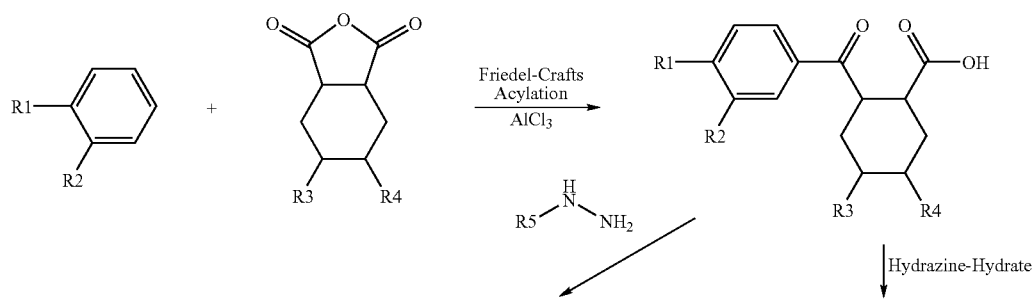

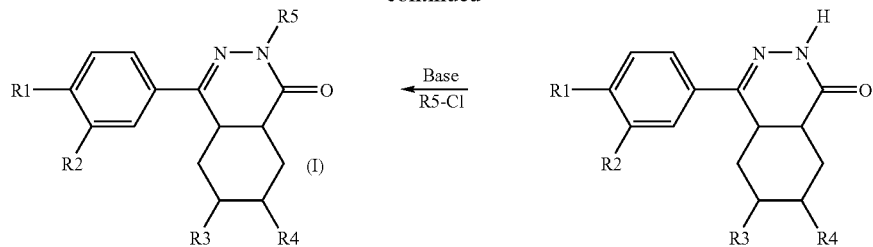
Compounds, in which R5 stands for R12 preferably prepared according to reaction scheme 2.
Reaction scheme 2:
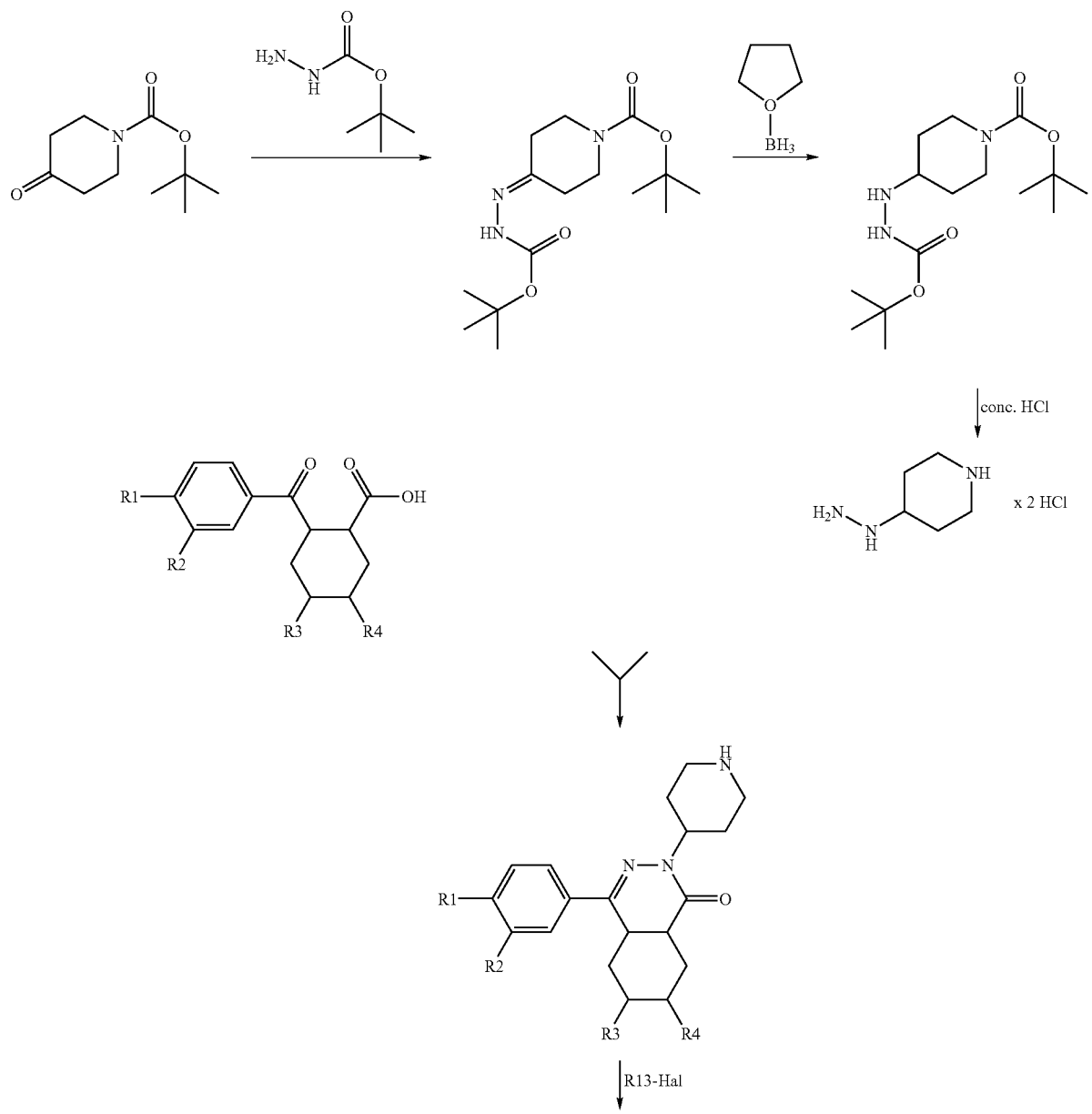

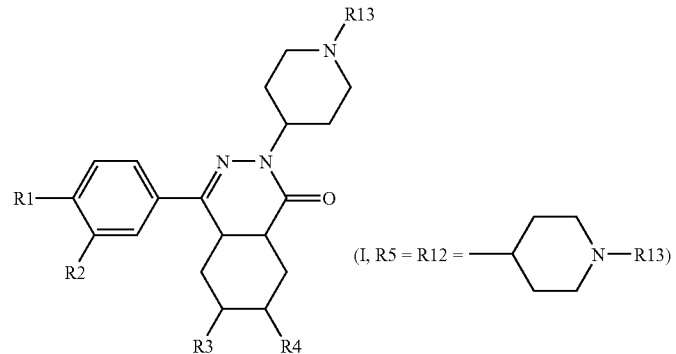
Compounds, in which R5 stands for R26 are preferably prepared according to reaction scheme 3.
Reaction scheme 3:
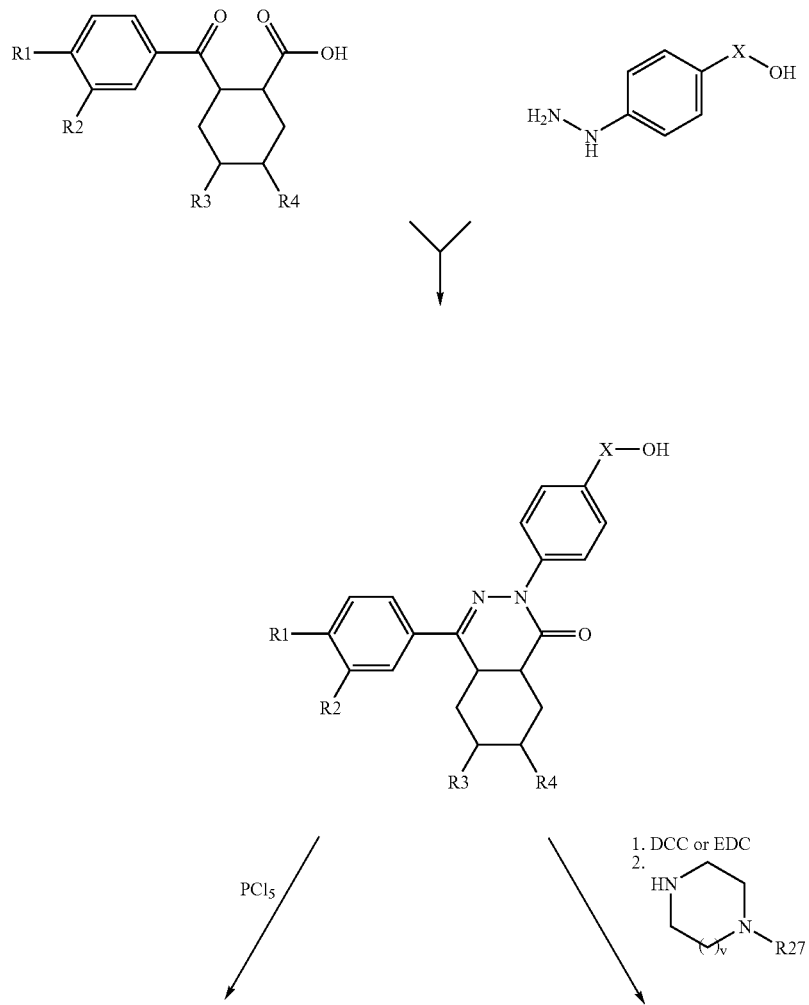

-continued

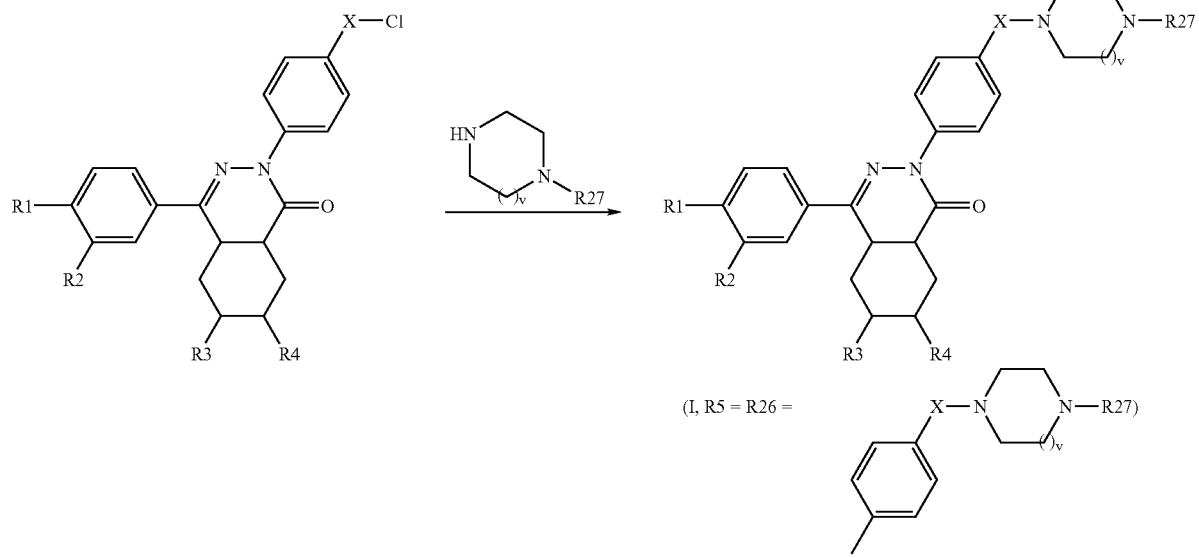

(I, R5 = R26 =)

Suitably, the conversions are carried out analogous to methods which are familiar per se to the person skilled in the art, for example, in the manner which is described in the following examples.

The substances according to the invention are isolated and purified in a manner known per se, e.g. by distilling off the solvent in vacuo and recrystallising the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula I, of which the preparation is explicitly not described, can be prepared in an analogous way or in a way which is known by a person skilled in the art using customary preparation methods.

The compounds, which are mentioned in the examples as well as their salts are preferred compounds of the invention.

EXAMPLES

Final Products 1. (cis)-4-(3-Chloro-4-methoxy-phenyl)-2-[1-(1-morpholin-4-yl-methanoyl)-piperidin-4-yl]-4a,5,8,8a-tetrahydro-2H-phthalazin-1-one A solution of 1.0 g of intermediate product A1 and 1.0 g of morpholine-4-carbonyl chloride in 50 ml of pyridine is stirred at RT for 18 h after which the mixture is evaporated. The residue is partitioned between aqueous sodium carbonate and dichloromethane. The dichloromethane layer is dried over magnesium sulfate and evaporated. The compound is crystailised from diethyl ether. M. p. 185–186° C.

2. (cis)-4-(3-Chloro-4-methoxy-phenyl)-2-[1-(toluene-4-sulfonyl)-piperidin-4-yl]-4a,5,8,8a-tetrahydro-2H-phthalazin-1-one A solution of 1.0 g of intermediate product A1 and 1.0 g of p-toluenesulfonyl chloride in 50 ml of pyridine is stirred at RT for 18 h after which the mixture is evaporated. The residue is partitioned between aqueous sodium carbonate and dichloromethane. The dichloromethane layer is dried over magnesium sulfate and evaporated. Crystallised from a mixture of ethyl acetate and petroleum ether (60-80° C.). M. p. 198–199° C.

3. (cis)-2-(1-Acetyl-piperidin-4-yl)-4-(3-chloro-4-methoxy-phenyl)-4a,5.8,8a-tetrahydro-2H-phthalazin-1-one A solution of 1.0 g of intermediate product A1 and 1.0 g of acetic anhydride in 50 ml of pyridine is stirred at RT for 18 h after which the mixture is evaporated. The residue is partitioned between aqueous sodium carbonate and dichloromethane. The dichloromethane layer is dried over magnesium sulfate and evaporated. Crystallised from ethyl acetate. M. p. 206–208° C.

4. (cis)-4-(3-Chloro-4-methoxy-phenyl)-2-(1-pyridin-4-ylmethyl-piperidin-4-yl)-4a,5,8,8a-tetrahydro-2H-phthalazin-1-one hydrochloride A mixture of 1.0 g of intermediate product A1, 1.0 g of 4-picolylchloride hydrochloride and 1.0 g of potassium carbonate in 20 ml of dimethylformamide is stirred for 18 h at RT after which 100 ml of water is added to the reaction mixture. The mixture is extracted with diethyl ether. The ether solution is dried over magnesium sulfate. After the addition of a saturated solution of hydrochloric acid in ether, the compound precipitated. M. p. 244° C. (decomposition).

5. (cis)-4-(3-Chloro-4-methoxy-phenyl)-2-(4-{1-[4-(2-dimethylamino-ethyl)-piperazin-1-yl]-methanoyl}-phenyl)-4a,5,8,8a-tetrahydro-2H-phthalazin-1-one dihydrochloride A mixture of 2 mmol of intermediate product A2, 2 mmol of 1-(2-dimethylaminoethyl)-piperazine and 3 mmol of 1-(3-dimethylaminopropyl)-3-ethylcarbodiimide hydrochloride in 30 ml of dimethylformamide is stirred for 18 h, after which the mixture is poored into aqueous sodium carbonate. This mixture is extracted with diethyl ether and the extract is dried over magnesium sulfate. Addition of a solution of hydrochloric acid in ether causes precipitation of the title compound. M. p.198–201° C.

6. (cis)-4-(3-Chloro-4-methoxy-phenyl-2-(6-methyl-3-trifluoromethyl-pyridin-2-yl)-4a,5,8,8a-tetrahydro-2H-phthalazin-1-one A solution of 12 mmol of 6-methyl4trifluoromethyl-pyridin-2-yl)hydrazine, 10 mmol of starting compound A6 and 1 g of pyridine hydrochloride in 50 ml of pyridine is refluxed for 18 h after which the solvent is evaporated. The residue is dissolved in dichloromethane and this solution is washed with 1N hydrochloric acid. The organic phase is dried over magnesium sulfate and evaporated. The residue is crystallised from diethyl ether. M. p. 156–157° C.

7. (cis)-2-Benzothiazol-6-yl-4-(3-chloro-4-methoxy-phenyl)-4a,8,8a-tetrahydro-2H-phthalazin-1-one A solution of 12 mmol of benzothiazol-6-ylhydrazine, 10 mmol of starting compound A6 and 1 g of pyridine hydrochloride in 50 ml of pyridine is refluxed for 18 h after which the solvent is evaporated. The residue is dissolved in dichloromethane and this solution is washed with 1N hydrochloric acid. The organic phase is dried over magnesium sulfate and evaporated. The residue is crystallised from diethyl ether. M. p. 156–157° C.

8. (cis)-4-(3-Chloro-4-methoxy-phenyl)-2-(1-oxo-1,3-dihydro-isobenzofuran-5-yl)-4a,5,8,8a-tetrahydro-2H-phthalazin-1-one A solution of 12 mmol of 5-hydrazino-3H-isobenzofuran-1-one, 10 mmol of starting compound A6 and 1 g of pyridine hydrochloride in 50 ml of pyridine is refluxed for 18 h after which the solvent is evaporated. The residue is dissolved in dichloromethane and this solution is washed with 1N hydrochloric acid. The organic phase is dried over magnesium sulfate and evaporated. The residue is crystallised from diethyl ether. M. p. 212–213° C.

9. (cis)-4-(3-Chloro-4-methoxy-phenyl)-2-(1H-indazol-5-yl)-4a,5,8,8a-tetrahydro-2H-phthalazin-1-one hydrochloride A solution of 12 mmol of 1H-indazol-5-ylhydrazine, 10 mmol of starting compound A6 and 1 g of pyridine hydrochloride in 50 ml of pyridine is refluxed for 18 h after which the solvent is evaporated. After evaporating the pyridine, the residue is dissolved in ethyl acetate and washed with aqueous sodium carbonate. The solvent is dried over magnesium sulfate and evaporated. The residue is dissolved in ethyl acetate and to this solution, a solution of hydrochloric acid in ether is added. The precipitate is filtered off and dried. M p. 196-197° C.

10. (cis)-4-(3Chloro-4-methoxy-phenyl)-2-cyclopentyl-4a,5,8,8a-tetrahydro-2H-phthalazin-1-one 12 mmol of sodium hydride is added to a solution of 10 mmol of intermediate product A3 in 50 ml of DMF. The resulting mixture is stirred for 30 min after which 10 mmol of chlorocyclopentane is added. The resulting mixture is stirred for 1 h and subsequently poured into water. The precipitate is filtered off and crystallised from methanol. M. p. 201–202° C.

11. (cis)-4-(3-Chloro-4-methoxy-phenyl)-2-(4-imidazol-1-yl-butyl)-4a,5,8,8a-tetrahydro-2H-phthalazin-1-one hydrochloride A mixture of 5 mmol of intermediate product A4 and 20 mmol of imidazole in 20 ml of DMF is stirred for 18 h at RT after which the solution is poured into aqueous sodium carbonate. This solution is extracted with diethyl ether. After drying over magnesium sulfate, a solution of hydrochloric acid in ether is added. The precipitate is filtered off and dried. M. p. 217–219° C.

12. (cis)-4-{4-[4-(3-Chloro-4-methoxy-phenyl)-1-oxo-4a,5,8,8a-tetrahydro-1H-phthalazin-2-yl]-butoxy}benzoic acid A solution of 5 mmol of intermediate product A4, 5 mmol of 4-hydroxybenzoic acid and 20 mmol of potassium carbonate in 50 ml of DMF is stirred for 18 h at RT after which the solution is poured into water. This aqueous solution is washed with diethyl ether twice and subsequently acidified with hydrochloric acid. The acidified solution is extracted with diethyl ether (3×) and the organic solution is dried over magnesium sulfate. The compound crystallised on concentrating under reduced pressure. M. p. 169–171° C.

13. (cis)-4-[4-(3-Fluoro-4-methoxy-phenyl)-1-oxo-4a,5,8,8a-tetrahydro-1H-phthalazin-2-yl]-benzoic acid A solution of 12 mmol of 4hydrazinobenzoic acid, 10 mmol of starting compound A5 and 1 g of pyridine hydrochloride in 50 ml of pyridine is refluxed for 18 h after which the solvent is evaporated. The residue is dissolved in dichloromethane and this solution is washed with 1N hydrochloric acid. The organic phase is dried over magnesium sulfate and evaporated. The residue is crystallised from diethyl ether. M p. 201–203° C.

14. (cis)-4-{4-(3-chloro-4-methoxyphenyl)-1-oxo-4a,5,8,8a-tetrahydro-1H-phthalazin-2-yl}-benzoic acid A solution of 8 g of starting compound A6 and 8 g of 4-hydrazinobenzoic acid in a mixture of 100 ml of 1-propanol and 5 ml of triethylamine is refluxed for 18 h. After evaporating the solvent, the residue is partitioned between diluted hydrochloric acid and dichloromethane. The organic layer is dried over magnesium sulfate and evaporated. The residue is purified by chromatography (ethyl acetate). Crystallisation from diethyl ether. M. p. 222–224° C.

15. (cis)-4-{4-(3-bromo-4-methoxyphenyl)-1-oxo-4a,5,8,8a-tetrahydro-2H-phthalazin-2-yl}-benzoic acid Prepared from 4-hydrazinobenzoic acid and starting compound A10 as described for compound 13.
M. p. 231–234° C.

16. (cis)-4-(3-chloro-4-methoxy-phenyl)-2-quinoxalin-2-yl-4a,5,8,8a-tetrahydro-2H-phthalazin-1-one Prepared from quinoxalin-2-yl-hydrazine and starting compound A6 as described for compound 7. M. p. 172–174° C.

17. (cis)-4-(3-Chloro-4-methoxy-phenyl)-2-(1,3,4-trimethyl-1H-pyrazolo[3,4-b]pyridin-6-yl)-4a,5,8,8a-tetrahydro-2H-phthalazin-1-one Prepared from (1,3,4-trimethyl-1H-pyrazolo[3,4-b]pyridin-6-yl)-hydrazine and starting compound A6 as described for compound 7. M. p. 217–219° C.

18. (cis)-4-(3-Chloro-4-methoxy-phenyl)-2-(3-thiophen-2-yl-[1,2,4]thiadiazol-5-yl)-4a,5,8,8a-tetrahydro-2H-phthalazin-1-one Prepared from (3-thiophen-2-yl-[1,2,4]thiadiazol-5-yl)-hydrazine and starting compound A6 as described for compound 7. M. p. 254–256° C.

19. (cis)-4-(3-Chloro-4-methoxy-phenyl)-2-(1,1-dioxo-tetrahydro-1 $1^6$-thiophen-3-yl)-4a,5,8,8a-tetrahydro-2H-phthalazin-1-one Prepared from (1,1-dioxo-tetrahydro-1$1^6$-thiophen-3-yl)-hydrazine and starting compound A6 as described for compound 7. M. p. 181–184° C.

20. (cis)-4o-3-Chloro -4nethoxy- phenyl)-2-phenyl-4a,5,8,8a-tetrahydro-2H-phthalazin-1-one Prepared from phenythydrazine and starting compound A11 as described for compound 7. M. p. 161–162° C.

21. (cis)-4-(3-Chloro-4-methoxy-phenyl)-2-phenyl-4a,5,8,8a-tetrahydro-2H-phthalazin-1-one Prepared from phenylhydrazine and starting compound A6 as described for compound 7. M. p. 151–152° C.

22. cis-4-(3-Chloro-4-methoxy-phenyl)-2-{1-[1-(2-oxo-imidazolidin-1-yl)-methanoyl]-piperidin-4-yl}-4a,5,8,8a-tetrahydro-2H-phthalazin-1-one Prepared from intermediate product A1 and 2-oxo-imidazolidine-1-carbonyl chloride as described for compound 1. M. p. 216–218° C.

Starting Compounds and Intermediate Products:

A1. (cis)-4-(3-Chloro-4-methoxy-phenyl)-2-piperidin-4-yl-4a,5,8,8a-tetrahydro-2H-phthalazin-1-one A solution of 50 mmol of starting compound A6, 55 mmol of piperidin-4-yl-hydrazine dihydrochloride (intermediate product A7) and 100 mmol of triethylamine in 150 ml of 1-propanol is refluxed for 18 h. After cooling to RT, the precipitate is filtered off and dried. M. p. 268–270° C.

A2. (cis)-4-{4-(3-chloro-4-methoxyphenyl)-1-oxo-4a,5,8,8a-tetrahydro-1H-phthalazin-2-yl}-benzoic acid A solution of 8 g of starting compound A6 and 8 g of 4-hydrazinobenzoic acid in a mixture of 100 ml of 1-propanol and 5 ml of triethylamine is refluxed for 18 h. After evaporating the solvent, the residue is partitioned between diluted hydrochloric acid and dichloromethane. The organic layer is dried over magnesium sulfate and evaporated. The residue is purified by chromatography (ethyl acetate). Crystallisation from diethyl ether. M. p. 222–224° C.

A3. (cis)-4-(3-chloro-4-methoxy-phenyl)-4a,5.8.8a-tetrahydro-2H-phthalazin-1-one A solution of 50 mmol of starting compound A6 and 0.1 mol of hydrazine hydrate in 100 ml of ethanol is refluxed for 5 h. On cooling to RT the compound precipitated. M. p. 201–204° C.

A4. (cis)-2-(4-bromo-butyl)-4-(3-chloro-4-methoxy-phenyl)-4a,5,8,8a-tetrahydro-2H-phthalazin-1-one 12 mmol of sodium hydride is added to a solution of 10 mmol of intermediate product A3 in 50 ml of DMF. The resulting mixture is stirred for 30 min after which 50 mmol of 1,4-dibrombutane is added. The resulting mixture is stirred for 1 h and subsequently poured into water. Purified by chromatography (ethyl acetate:hexane/1:4) and crystallised from hexane. M. p. 109–111° C.

A5. (cis)-2-(3-fluoro-4-methoxybenzoyl)-1,2,3,6-tetrahydrobenzoic acid

Prepared analogously to starting compound A6 as described in WO99/47505 using 2-fluoroanisole instead of 2-chloroanisole. M. p. 185–187° C.

A6. (cis)-2-(3-chloro-4methoxybenzoyl)-1,2,3,6-tetrahydrobenzolc acid

Prepared as described in WO99/47505.

A7. Piperidin-4-yl-hydrazine dihydrochloride

A mixture of 0.1 mole of 4-(N'-tert-Butoxycarbonyl-hydrazinoypiperidine-1-carboxylic acid tert-butyl ester (intermediate product A8) and 150 ml of concentrated hydrochloric acid is heated at 90° C. for 60 min after which the clear solution is evaporated. The residue is washed with tetrahydrofurane, filtered off and dried under vacuum. M. p. 256–259° C.

A8. 4-(N'-tert-Butoxycarbonyl-hydrazino)-piperidine-1-carboxylic acid tert-butyl ester 150 ml of a solution of borohydride in tertahydrofurane (1.0 mol/l) is slowly added to a solution of 0.12 mole of 4-(tert-Butoxycarbonyl-hydrazono)-piperidine-1-carboxylic acid tert-butyl ester (intermediate product A9) in 100 ml of dry tetrahydrofurane. After complete addition, the mixture is stirred for another 30 min after which a 100 ml of water is added to destroy the excess of borohydride. Subsequently the tetrahydrofurane is evaporated and the resulting aqeous solution extracted with diethyl ether. After drying the solvent over magnesium sulfate, the ether is evaporated. M. p.112–115° C.

A9. 4-(tert-Butoxycarbonyl-hydrazono)-piperidine-1-carboxylic acid tert-butyl ester A mixture of 0.15 mole of 4-oxo-piperidine-1-carboxylic acid tert-butyl ester (commercially available) and 0.15 mole of tert-butylcarbazate in 250 ml of hexane is stirred for 18 h at RT. The precipitate is filtered off and dried under vacuum. M. p. 172–174° C.

A10. (cis)-2-(3-bromo-4-methoxybenzoyl)-1,2,3,6-tetrahydrobenzoic acid

Prepared analogously to starting compound A6 as described in WO99/47505 using 2-bromoanisole instead of 2-chloroanisole. M. p. 201–204 ° C.

A11. (cis)-2-(3-chloro-4-ethoxybenzoyl)-1,2,3,6-tetrahydrobenzoic acid

Prepared analogously to starting compound A6 as described in WO99/47505 using 1-chloro-2-ethoxybenzene instead of 2-chloroanisole. M. p.123–125° C.

COMMERCIAL UTILITY

The second messenger cyclic AMP (CAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21–40, "The Handbook of Immunopharmacology", Academic Press, 1996), and its inhibition leads to an increase of the intracellular cAMP concentration and thus to the inhibition of cellular activation (J E Souness et al., Immunopharnacology 47: 127–162, 2000).

The antiinflammatory potential of PDE4 inhibitors in vivo in various animal models has been described (M M Teixeira, TiPS 18: 164–170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682–690, 1991) or eosinophilic (A Hatzelmann et al., Brit J Pharmacol 114: 821–831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221–231, 1997, and Pulmonary Pharmacol Therap 12: 377–386, 1999). In addition, the immunomodulatory potential of PDE4 inhibitors is evident from the inhibition of T-cell responses like cytokine synthesis or proliferation (DM Essayan, Biochem Pharmacol 57: 965–973, 1999). Substances which inhibit the secretion of the afore-mentioned proinflammatory mediators are those which inhibit PDE4. PDE4 inhibition by the compounds according to the invention is thus a central indicator for the suppression of inflammatory processes.

Of the 11 phosphodiesterase (PDE) isoenzymes which are presently known, PDE7 was described for the first time, as HCP1 ("high affinity cAMP-specific PDE"), in 1993 (Michaeli T, Bloom T J, Martins T, Loughney K, Ferguson K, Riggs M, Rodgers L, Beavo J A and Wigler M, Isolation and characterization of a previously undetected human cAMP phosphodiesterase by complementation of cAMP phosphodiesterase-deficient *Saccharomyces cerevisiae*, J Biol Chem 268: 12925–12932, 1993). According to today's nomenclature, HCP1 is human PDE7A1; in addition to this, another human splicing variant of the same gene (PDE7A 2) (Han P, Zhu X and Michaeli T, Alternative splicing of the high affinity cAMP-specific phosphodiesterase (PDE7A) mRNA in human skeletal muscle and heart. J Biol Chem 272: 16152–16157, 1997) and a second human PDE7 gene (PDE7B) (Sasaki T, Kotera J, Yuasa K and Omori K, Identification of human PDE7B, a cAMP-specific phosphodiesterase Biochem Biophys Res Commun 271: 575–583, 2000) were described in the subsequent years. Individual representatives of the PDE7 isoenzyme are characterized by being particularly prominently expressed in specific areas of the brain (putamen, caudate nucleus), in skeletal muscle, in leukaemic T cell lines and in naive CD4+ T cells. The induction of PDE7 has been described as being an essential prerequisite for activating T cells (Li L, Yee C and Beavo J A, CD3- and CD28-dependent induction of PDE7 required for T cell activation. Science 283: 848–851, 1999).

The compounds according to the invention have useful pharmacological properties which make them industrially utilizable. As selective cyclic nucleotide phosphodiesterase (PDE) inhibitors (specifically of type 4 and 7), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, T-cells, interleukins, chemokines, alpha-, beta- and gamma-interferon, tumor necrosis factor (TNF) or oxygen free radicals and proteases.

On account of their PDE-inhibiting properties, the compounds according to the invention can be employed in human and veterinary medicine as therapeutics, where they can be used, for example, for the treatment and prophylaxis of the following Illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative coltis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctiyltis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

Particularly on account of their PDE7-inhibiting properties, the compounds according to the invention are suitable for treating T-cell mediated diseases of inflammatory nature, for example of the kidney (glomerulonephritis) or of the pancreas (autoimmune diabetes) and, furthermore, for inhibiting the degenerative proliferation of T cells in various forms of T cell leukaemia. In addition, the said compounds are of potential value in treating certain diseases of the brain (such as epilepsy) and of the skeletal muscle (such as muscular atrophy).

The compounds according to the invention are distinguished by a low toxicity, a good enteral absorption (high bioavailability), a large therapeutic breadth and the absence of significant side effects.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterases of type 4 and 7 (PDE4/7), ameliorating the symptoms of an PDE4- and/or PDE7-mediated disorder, and wherein the packaging material comprises a label or package insert which indicates that the pharmaceutical agent is useful for preventing or treating PDE4- and/or PDE7-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The medicaments are prepared by processes which are known per se and familiar to the person skilled in the art. As medicaments, the compounds according to the invention (=active compounds) are either employed as such, or preferably in combination with suitable pharmaceutical auxiliaries and/or excipients, e.g. In the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the medicaments according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patent. In addition to the use of adaptors (spacers, expanders) and pear-shaped containers (e.g. Nebulator®, Volumatic®), and automatic deylces emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg/kg per day.

Biological Investigations

Method for Measuring Inhibition of PDE4 and PDE7 Activities

The cDNA for PDE7A1 (Genebank Acc. No. L12052) was isolated, using RT-PCR, from total cellular RNA derived from the T cell line CCRF-CEM and cloned into the cloning vector pCR2.1 (invitrogen, Groningen, NL) under standard conditions (the manufacturer's instructions). For expression in insect cells, the cDNA was subcloned into the baculo expression vector pCRBac (invitrogen, Groningen, NL). The cDNA for PDE4D3 was a gift of Marco Conti (Stanford University, USA). The ORF (Genebank Acc. No. U50159) was cut from the original pCMV5 vector with the restriction enzymes EcoRI and XbaI and subcloned in the expression vector pBacPak9 (Clontech, Palo Alto).

The recombinant baculoylrus was prepared by means of homologous recombination in SF9 insect cells. The expression plasmids were cotransfected with Bac-N-Blue (invitrogen, Groningen, NL) or Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDEs were expressed in SF21 cells by infecting $2 \times 10^6$ cells/ml with an MOI (multiplicity of infection) between 2 and 5 in serum-free SF900 medium (Life Technologies, Paisley, UK). The cells were cultured at 28° C. for 48 hours, after which they were pelleted for 5–10 min at 1000 g and 4° C. In the case of PDE7A1 cells were cultured in spinner flasks at a rotational speed of 75 rpm.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 1 mM β-mercaptoethanol, 2 mM benzamidine, 0.4 mM Pefablock, 10 μM leupeptin, 10 μM pepstatin A, 5 μM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE7A1 and PDE4D3 activities were inhibited by the said compounds in a modified SPA (scintillation proximity assay) test, supplied by Amersham Pharmacia Biotech (see procedural instructions "phosphodiesterase [3H]cAMP SPA enzyme assay, code TRKQ 7090"), carried out in 96-well microtitre plates (MTP's). The test volume is 100 μl and contains 20 mM Tris buffer (pH 7.4), 0.1 mg of BSA (bovine serum albumin)/ml, 5 mM $Mg^{2+}$, 0.5 μM cAMP (including about 50,000 cpm of [3H]cAMP), 2 μl of the respective substance dilution in DMSO and sufficient recombinant PDE (1000×g supernatant, see above) to ensure that 15–20% of the cAMP is converted under the said experimental conditions. After a preincubation of 5 min at 37° C., the reaction is started by adding the substrate (cAMP) and the assays are incubated for a further 15 min; after that, they are stopped by adding SPA beads (50 μl). In accordance with the manufacturer's instructions, the SPA beads had preylously been resuspended in water and then diluted 1:3 (v/v); the diluted solution also contains 3 mM IBMX. After the beads have been sedimented (>30 min), the MTP's are analyzed in commercially available measuring appliances and the corresponding IC50 values of the compounds for the inhibition of PDE activities are determined from the concentration-effect curves by means of non-linear regression.

The inhibitory values determined for the compounds according to the invention follow from the following table A, in which the numbers of the compounds correspond to the numbers of the examples.

TABLE A

Inhibition of PDE4 and PDE7 acitivity
[measured as $-\log IC_{50}$ (mol/l)]

| Compound | PDE4<br>$-\log IC_{50}$ (mol/l) | PDE7<br>$-\log IC_{50}$ (mol/l) |
| --- | --- | --- |
| 1 | 8.64 | 7.64 |
| 2 | 8.4 | 6.97 |
| 3 | 8.25 | 6.74 |
| 4 | 8.61 | 7.38 |
| 5 | 7.86 | 7.18 |
| 6 | 7.64 | 7.08 |
| 7 | 8.09 | 6.98 |
| 8 | 8.05 | 7.05 |
| 9 | 8.59 | 7.54 |
| 10 | 9.11 | 7.73 |
| 11 | 9.05 | 6.57 |
| 12 | 8.19 | 7.01 |
| 13 | 7.34 | 6.42 |
| 17 | 7.66 | 7.38 |
| 18 | 7.63 | 7.11 |

What is claimed is:
1. A compound of formula I

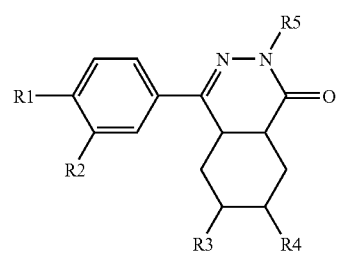

in which
  R1 is methoxy or ethoxy,
  R2 is chlorine, bromine or fluorine
  R3 and R4 together form an additional bond,
  R5 is R6, —$C_mH_{2m}$—R7, —$C_pH_{2p}$—Y-Aryl1, R12 or R26 in which
  R6 3-6C-cycloalkyl, 3-7C-cycloalkylmethyl, quinoxalinyl, indazolyl, benzothiazolyl, 6-methyl-3-trifluoromethyl-pyridin-2-yl, 1,3,4-trimethyl-1H-pyrazolo[3,4-b]pyridin-6-yl, 3-thiophen-2-yl[1,2,4]-thiadiazol-5-yl, 1,1-dioxide-tetrabydrothiophen-3-yl, 1-oxo-1,3-dihydroisobenzofuran-5-yl, 4-(4-yl-but-1-oxy)-benzoic acid, or an unsubstituted or by R61 substituted phenyl radical, in which
  R61 is 1-4C-alkyl, 1-4C-alkoxy, carboxyl or 1-4C-alkoxycarbonyl, R7 is carboxyphenyloxy,
Y is a bond,
Aryl1 is imidazolyl,
m is an integer from 1 to 4,
p is an integer from 1 to 4,
R12 is a radical of formula (a)

(a)

wherein
R13 is —S(O)₂—R14, —C(O)R17 or Aryl3-1-4C-alkyl,
R14 is phenyl or phenyl substituted by R22,
R17 is 1-4C-alkyl, 2-oxo-imidazolidin-1-yl or —N(R20)R21,
R20 and R21 are independent from each other 1-7C-alkyl, or R20 and R21 together and with inclusion of the nitrogen atom to which they are bonded, form a 4-morpholinyl-, 1-pyrrolidinyl-, 1-piperidinyl- or 1-hexahydroazepino-ring,
R22 is 1-4C-alkyl,
Aryl3 is pyridyl,
R26 is a radical of formula (c)

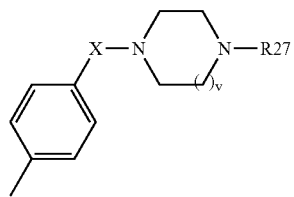

(c)

wherein
R27 is —(CH₂)ᵤR30,
R30 is —N(R32)R33,
R32 is 1-4C-alkyl,
R33 is 1-4C-alkyl,
or R32 and R33 together and with inclusion of the nitrogen atom to which they are bonded, form a 4-morpholinyl-, 1-pyrrolidinyl-, 1-piperidinyl- or 1-hexahydroazepinyl-ring,
u is an integer from 1 to 4,
v is 1,
X is —C(O)—,
or a salt of thereof.

2. A compound of formula I according to claim 1 in which
R1 is methoxy or ethoxy,
R2 is chlorine, bromine or fluorine,
R3 and R4 together form an additional bond,
R5 is 1-(morpholin-4-yl-methanoyl)-piperidin-4-yl, 1-(toluene-4-sulfonyl)-piperidin-4-yl, 1-acetyl-piperidin-4-yl, 1-(pyridin-4-ylmethyl)-piperidin-4-yl, 4-{1-[4-(2-dimethylamino-ethyl)-piperazin-1-yl]-methanoyl}-phenyl, quinoxalin-2-yl, 6-methyl-3-trifluoromethyl-pyridin-2-yl, 1,3,4-trimethyl-1H-pyrazolo[3,4-b]pyridin-6-yl, phenyl, 3-thiophen-2-yl[1,2,4]thiadiazol-5-yl, 1,1-dioxide-tetrahydrothiophen-3-yl, benzothiazol-6-yl, 1-oxo-1,3-dihydro-isobenzofuran-5-yl, 1H-indazol-5-yl, cyclopentyl, 4-imidazol-1-yl-butyl, 4-(4-yl-but-1-oxy)-benzoic acid, 4-hydroxycarbonylphenyl or 1-[1-[2-oxo-imidazolidin-1-yl)methanoyl]piperidin-4-yl,
or a salt thereof.

3. A compound of formula I according to claim 1 in which
R1 is methoxy or ethoxy,
R2 is chlorine,
R3 and R4 together form an additional bond,
R5 is 1-(morpholin-4-yl-methanoyl)-piperidin-4-yl, 1-(toluene-4-sulfonyl)-piperidin-4-yl, 1-acetyl-piperidin-4-yl, 1-(pyridin-4-ylmethyl)-piperidin-4-yl, 4-{1-[4-(2-dimethylamino-ethyl)-piperazin-1-yl]-methanoyl}-phenyl, quinoxalin-2-yl, 6-methyl-3-trifluoromethyl-pyridin-2-yl, 1,3,4-trimethyl-1H-pyrazolo[3,4-b]pyridin-6-yl, phenyl, 3-thiophen-2-yl[1,2,4]thiadiazol-5-yl, 1,1-dioxide-tetrahydrothiophen-3-yl, benzothiazol-6-yl, 1-oxo-1,3-dihydro-isobenzofuran-5-yl, 1H-indazol-5-yl, cyclopentyl, 4-imidazol-1-yl-butyl, 4-(4-yl-but-1-oxy)-benzoic acid, 4-hydroxycarbonylphenyl or 1-[1-[2-oxo-imidazolidin-1-yl)methanoyl]piperidin-4-yl,
or a salt thereof.

4. A compound of formula I according to claim 1 selected from the group consisting of
(cis)-4-(3-Chloro-4-methoxy-phenyl)-2-[1-(1-morpholin-4-yl-methanoyl)-piperidin-4-yl]-4a,5,8,8a-tetrahydro-2H-phthalazin-1-one,
(cis)-4-(3-Chloro-4-methoxy-phenyl)-2-[1-(toluene-4-sulfonyl)-piperidin-4-yl]-4a,5,8,8a-tetrahydro-2H-phthalazin-1-one,
(cis)-2-(1-Acetyl-piperidin-4-yl)-4-(3-chloro-4-methoxyphenyl)-4a,5,8,8a-tetrahydro-2H-phthalazin-1-one,
(cis)-4-(3-Chloro-4-methoxy-phenyl)-2-(1-pyridin-4-yl-methyl-piperidin-4-yl)4a,5,8,8a-tetrahydro-2H-phthalazin-1-one,
(cis)-4-(3-Chloro-4-methoxy-phenyl)-2-(4-{1-[4-(2-dimethylamino-ethyl)-piperazin-1-yl]-methanoyl}-phenyl)-4a,5,8,8a-tetrahydro-2H-phthalazin-1-one,
(cis)-4-(3-Chloro-4-methoxy-phenyl)-2-(6-methyl-3-trifluoromethyl-pyridin-2-yl)-4a,5,8,8a-tetrahydro-2H-phthalazin-1-one,
(cis)-2-Benzothiazol-6-yl-4-(3-chloro-4-methoxy-phenyl)-4a,5,8,8a-tetrahydro-2H-phthalazin-1-one,
(cis)-4-(3-Chloro-4-methoxy-phenyl)-2-(1-oxo-1,3-dihydro-isobenzofuran-5-yl)-4a,5,8,8a-tetrahydro-2H-phthalazin-1-one,
(cis)-4-(3-Chloro-4-methoxy-phenyl)-2-(1H-indazol-5-yl)4a,5,8,8a-tetrahydro-2H-phthalazin-1-one,
(cis)-4-(3-Chloro-4-methoxy-phenyl)-2-cyclopentyl-4a,5,8,8a-tetrahydro-2H-phthalazin-1-one,
(cis)-4-(3-Chloro-4-methoxy-phenyl)-2-(4-imidazol-1-yl-butyl)-4a,5,8,8a-tetrahydro-2H-phthalazin-1-one,
(cis)-4-{4-[4-(3-Chloro-4-methoxy-phenyl)-1-oxo-4a,5,8,8a-tetrahydro-1H-phthalazin-2-yl]-butoxy}-benzoic acid,
(cis)-4-[4-(3-Fluoro-4-methoxy-phenyl)-1-oxo-4a, 5,8, 8a-tetrahydro-1H-phthalazin-2-yl]-benzoic acid,
(cis)-4-{4-(3-chloro-4-methoxyphenyl)-1-oxo-4a,5,8,8a-tetrahydro-1H-phthalazin-2-yl}benzoic acid,
(cis)-4-{4-(3-bromo-4-methoxyphenyl)-1-oxo-4a,5,8,8a-tetrahydro-2H-phthalazin-2-yl}benzoic acid,
(cis)-4-(3-chloro-4-methoxy-phenyl)-2-quinoxalin-2-yl-4a,5,8,8a-tetrahydro-2H-phthalazin-1-one,
(cis)-4-(3-Chloro-4-methoxy-phenyl)-2-(1,3,4-trimethyl-1H-pyrazolo[3,4-b]pyridin-6-yl)-4a,5,8,8a-tetrahydro-2H-phthalazin-1-one,
(cis)-4-(3-Chloro-4-methoxy-phenyl)-2-(3-thiophen-2-yl-[1,2,4]thiadiazol-5-yl)-4a,5,8,8a-tetrahydro-2H-phthalazin-1-one, (cis)-4-(3-Chloro-4-methoxy-phenyl)-2-(1,1-dioxo-tetrahydro-1l(6)-thiophen-3-yl)-4a,5,8,8a-tetrahydro-2H-phthalazin-1-one, (cis)-4-(3-Chloro-4-ethoxy-phenyl)-2-phenyl-4a,5,8,8a-tetrahydro-2H-phthalazin-1-one, (cis)-4-(3-Chloro-4-methoxy-phenyl)-2-phenyl-4a,5,8,8a-tetrahydro-2H-phthalazin-1-one, (cis)-4-(3-Chloro-4-methoxy-phenyl)-2-{1-[1-(2-oxo-imidazolidin-1-yl)-methanoyl]-piperidin-4-yl}-4a,5,8,8a-tetrahydro-2H-phthalazin-1-one, and the salts of these compounds.

5. A compound of formula I according to claim 1 in which
R1 is methoxy or ethoxy,
R2 is chlorine,
R3 and R4 together form an additional bond,
R5 is 1-(1-morpholin-4-yl-methanoyl)-piperidin-4-yl, 1-(toluene-4-sulfonyl)-piperidin-4-yl, 1-acetyl-piperidin-4-yl, 1-(pyridin-4-ylmethyl)-piperidin-4-yl, 4-{1-[4-(2-dimethylamino-ethyl)-piperazin-1-yl]-methanoyl}-phenyl, quinoxalin-2-yl, 6-methyl-3-trifluoromethyl-pyridin-2-yl, 1,3,4 trimethyl-1H-pyrazolo[3,4-b]pyridin-6-yl, phenyl, 3-thiophen-2-yl [1,2,4]thiadiazol-5-yl, 1,1-dioxide-tetrahydrothiophen-3-yl, 2-benzothiazol-6-yl, 1-oxo-1,3-dihydro-isobenzofuran-5-yl, 1H-indazol-5-yl, cyclopentyl, 4-imidazol-1-yl-butyl, 4-(4-yl-but-1-oxy)-benzoic acid or hydroxycarbonylphen-4-yl, or a salt thereof.

6. A compound of formula I according to claim 1 in which
R1 is methoxy,
R2 is chlorine,
R3 and R4 together form an additional bond,
R5 is 1-(1-morpholin-4-yl-methanoyl)-piperidin-4-yl, 1-(toluene-4-sulfonyl)-piperidin-4-yl, 1-acetyl-piperidin-4-yl, 1-(pyridin-4-ylmethyl)-piperidin-4-yl, 4-{1-[4-(2-dimethylamino-ethyl)-piperazin-1-yl]-methanoyl}-phenyl, 6-methyl-3-trifluoromethyl-pyridin-2-yl, 2-benzothiazol-6-yl, 1-oxo-1,3-dihydro-isobenzofuran-5-yl, 1H-indazol-5-yl, cyclopentyl, 4-imidazol-1-yl-butyl, 4-(4-yl-but-1-oxy)-benzoic acid or hydroxycarbonylphen-4-yl, or a salt thereof.

7. A compound of formula I according to claim 1 in which the hydrogen atoms in the positions 4a and 8a are cis-configurated.

8. A compound of formula I according to claim 1 in which the absolute configuration (according to the rules of Cahn, ingold and Prelog) is S in the position 4a and R in the position 8a.

9. A method of treating a disease or disorder in a patient comprising administering to a patient in need thereof a compound of formula I according to claim 1, or a pharmacologically acceptable salt thereof, wherein the disease or disorder is selected from the group consisting of asthma, COPD, rheumatoid arthritis, psoriasis, atopic eczema and Crohn's disease.

10. A pharmaceutical composition comprising one or more compounds of formula I according to claim 1, or a pharmacologically acceptable salt thereof, together with a pharmaceutically acceptable auxiliaries or carrier material.

11. A method of treating an airway disorder in a patient comprising administering to a patient in need thereof an effective amount of a compound of formula I according to claim 1, or a pharmacologically acceptable salt thereof, wherein the disease or disorder is selected from the group consisting of asthma and COPD.

12. A method of treating a disease or disorder in a patient comprising administering to a patient in need thereof a compound of formula I according to claim 4, or a pharmacologically acceptable salt thereof, wherein the disease or disorder is selected from the group consisting of asthma, COPD, rheumatoid arthritis, psoriasis, atopic eczema and Crohn's disease.

13. A pharmaceutical composition comprising one or more compounds of formula I according to claim 4, or a pharmacologically acceptable salt thereof, together with a pharmaceutically acceptable excipient or carrier material.

14. A method of treating an airway disorder in a patient comprising administering to a patient in need thereof an effective amount of a compound of formula I according to claim 4, or a pharmacologically acceptable salt thereof, wherein the disease or disorder is selected from the group consisting of asthma and COPD.

* * * * *

UNITED STATES PATENT AND TRADEMARK OFFICE
CERTIFICATE OF CORRECTION

PATENT NO.       : 7,186,710 B2  
APPLICATION NO. : 10/475657  
DATED            : March 6, 2007  
INVENTOR(S)      : Sterk Page 1 of 1

It is certified that error appears in the above-identified patent and that said Letters Patent is hereby corrected as shown below:

Claim 1, Column 26, Line 62,  
delete

" 1,1-dioxide-tetrabydrothiophen-3-yl, " and replace with

-- 1,1-dioxide-tetrahydrothiophen-3-yl, --

Claim 8, Column 30, Line 6,  
delete

" ingold " and replace with

-- Ingold --

Claim 10, Column 30, Line 18,  
delete

" auxiliaries " and replace with

-- excipient --

Signed and Sealed this

First Day of May, 2007

JON W. DUDAS  
*Director of the United States Patent and Trademark Office*